US006436391B1

(12) United States Patent
Foster et al.

(10) Patent No.: US 6,436,391 B1
(45) Date of Patent: Aug. 20, 2002

(54) USE OF INTERFERON (IFN)-$\alpha_8$ AND -$\alpha_{14}$ AS VACCINE ADJUVANTS

(75) Inventors: Graham Russell Foster; Howard Christopher Thomas, both of London (GB)

(73) Assignee: Imperial College of Science, Technology & Medicine, London (GB)

( * ) Notice: Subject to any disclaimer, the term of this patent is extended or adjusted under 35 U.S.C. 154(b) by 0 days.

(21) Appl. No.: 08/897,235

(22) Filed: Jan. 31, 1997

(51) Int. Cl.[7] .................................................. A61K 38/21
(52) U.S. Cl. ...................................... 424/85.7; 424/278.1
(58) Field of Search ............................... 424/85.7, 278.1

(56) References Cited

U.S. PATENT DOCUMENTS 4,414,150 A  *  11/1983  Goeddel ..................... 424/85.4
4,820,514 A  *  4/1989   Cummins ................... 424/85.4
5,310,729 A  *  5/1994   Lernhardt ................... 514/15

FOREIGN PATENT DOCUMENTS

WO           95/24212      *  9/1995

OTHER PUBLICATIONS

Östlund, L., et al. Blood 67: 152–59, 1986.*
Evans, S.S., et al. J. Cell. Biol. 123 (6 Pt 2): 1889–98, 1993.*
Burke, F., et al. Hematol. Oncol. 11: 23–33, 1993.*
Imam, S.A., et al. Anticancer Res. 16: 1727–32, 1996.*

* cited by examiner

*Primary Examiner*—David L. Fitzgerald
(74) *Attorney, Agent, or Firm*—Nixon & Vanderhye

(57) ABSTRACT

The use of IFN-α subtypes as vaccine adjuvants is disclosed, together with vaccine compositions comprising them. Methods of vaccinating a subject comprising co-administration of IFN-α subtypes are also provided.

10 Claims, 1 Drawing Sheet

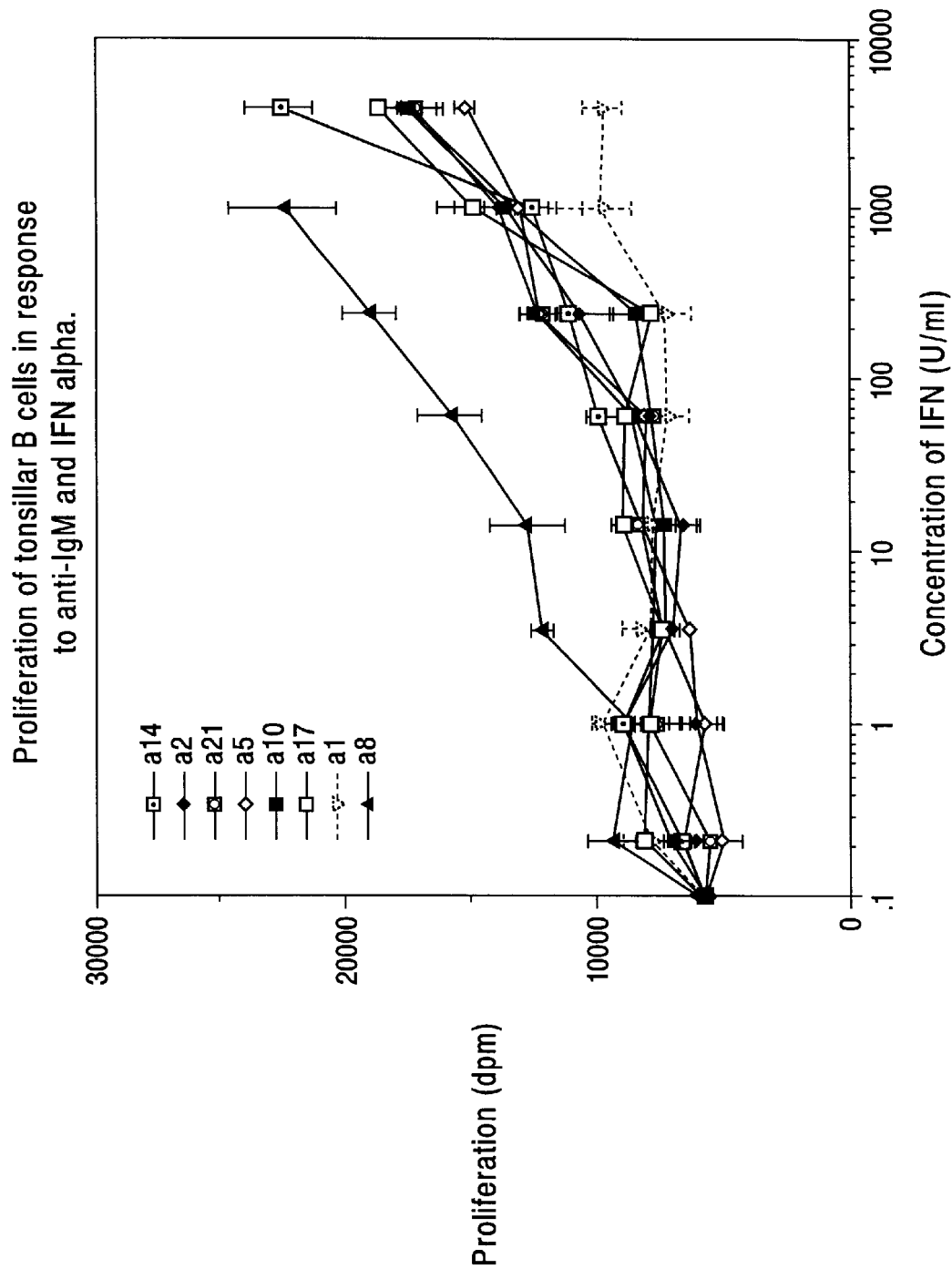

USE OF INTERFERON (IFN)-$\alpha_8$ AND -$\alpha_{14}$ AS VACCINE ADJUVANTS

The present invention relates to the use of Interferon-$\alpha$ subtypes, particularly IFN-$\alpha_8$, and/or IFN-$\alpha_1$, as adjuvants for vaccines. In addition, it relates to the use of these Interferon subtypes to stimulate proliferation of B lymphocytes.

Type I interferons (IFN) are a family of closely related glycoproteins containing many IFN-$\alpha$ subtypes and one IFN-$\beta$ subspecies. At least 23 different human IFN-$\alpha$ subtypes have been identified by analysis of human cDNA libraries and by protein analysis of the IFNs produced by stimulated lymphoblastoid cells. The reasons for this heterogeneity are not yet known. Previous studies have suggested that all Type I IFNs bind to an identical receptor and therefore have identical effects. However a mutant cell line that responds only to IFN-$\beta$ but not IFN-$\alpha$ has been identified showing that these two IFN subspecies bind to a different receptor and may therefore have different effects. Studies on the transmembrane human IFN receptor have shown that if this receptor is transfected into murine cells the cells respond only to some IFN subtypes, showing that a second receptor component is required to allow cells to respond to IFN and that the murine equivalent of this component is able to distinguish between different IFN subtypes. Molecular analysis of the human Type I IFN receptor thus suggests that the receptor may be able to distinguish between different IFN subtypes.

A number of studies have compared the effects of different IFN-$\alpha$ subtypes on the antiviral activities of human cell lines. Zoon et al (J. Biol. Chem. 267: 15210–16 (1992) studied IFNs that were obtained from HPLC purification of natural IFN and found no gross differences in their antiviral activities. However, Sperber et al, *J. Interferon. Res.* 12 363–368 (1992) examined the effects of different recombinant IFN-$\alpha$ subtypes on cells infected with the human immunodeficiency virus (HIV) and found marked differences in their antiviral properties. W)95/24212 disclosed that different IFN-$\alpha$ subtypes were effective antiviral agents in different cell types. Thus, it is possible to target viral infections in say the liver by the use of particular subtypes, eg IFN-$\alpha_8$.

B cells or B lymphocytes are a subset of lymphocytes found in secondary lymphoid organs as well as circulating in the blood. They are characterised by the possession of antigen-specific cell surfaceimmunoglobulin molecules of a single antigen-binding specificity which act as receptors for antigen. The interaction of antigen with the cell-surface immunoglobulin is in part responsible for subsequent proliferation of the B cells and their development into antibody-secreting plasma cells.

We have now found that B cell proliferation can be induced by certain IFN-$\alpha$ subtypes. Thus, it is possible to stimulate a subject's immune response and in particular the subtypes can be used as adjuvants to increase the effectiveness of vaccines.

Thus, in a first aspect the present invention provides an adjuvant for a vaccine comprising an IFN-$\alpha$ subtype. In particular the invention provides an adjuvant for a vaccine which comprises IFN-$\alpha_8$ and/or IFN-$\alpha_{14}$.

The adjuvant of the present invention can be co-administered with a vaccine or could itself form part of the vaccine itself. Thus, in a second aspect the present invention provides a vaccine comprising at least one IFN-$\alpha$ subtype, preferably IFN-$\alpha_8$ and/or IFN-$\alpha_{14}$.

The skilled person will appreciate that the particular antigen or antigens which the vaccine comprises is/are not important. Due to the ability of particular IFN-$\alpha$ subtypes to stimulate B cell proliferation they find general use as adjuvants and enable enhanced immune responses to be obtained upon vaccination.

In a third aspect the present invention provides a method of vaccinating a subject which comprises the step of co-administering to the subject an IFN-$\alpha$ subtype. As already discussed herein, the co-administration can be separate or the IFN-$\alpha$ subtype can be administered as part of the vaccine itself.

In a final aspect the present invention provides a method for stimulating proliferation of B cells which comprises the step of bringing one or more B cells into contact with at least one IFN-$\alpha$ subtype, preferably IFN-$\alpha_8$ and/or IFN-$\alpha_{14}$.

The invention will now be described by means of the following example which should not be construed as in any way limiting the invention.

The example refers to the FIGURE which shows proliferation of tonsillar B cells in response to anti-IgM and IFN-$\alpha$ subtypes.

EXAMPLE

Human tonsillar B lymphocytes were purified by Ficoll density gradient centrifugation followed by E resetting with sheep red blood cells (SRBC) to remove T cells. the resulting cells were cultured at $1 \times 10^6$ cells/ml in RPMI 1640 medium with 10% FCS and gentamycin for three days.

$^3$H thymidine was added for the last 8 hours of culture and incorporation was measured by scintillation counting. The cells were stimulated with anti-IgM conjugated to beads at 10 $\mu$g/ml and FPLC purified IFN-$\alpha$ subtypes.

The results (see FIGURE) show that all the IFN-$\alpha$ subtypes caused an increase in B cell proliferation, with the exception of IFN-$\alpha_1$, which is inactive at the concentrations used in the experiment. IFN-$\alpha_8$ and IFN-$\alpha_{14}$ were the most active in the assay, causing proliferation equivalent to that obtained with IL-4 in the same cells (data not shown).

What is claimed is:

1. A vaccine composition comprising an antigen and interferon (IFN)-$\alpha$ as an adjuvant, wherein the IFN-$\alpha$ consists essentially of IFN-$\alpha_8$ or a mixture of IFN-$\alpha_8$ and IFN-$\alpha_{14}$.

2. A vaccine composition according to claim 1, wherein the IFN-$\alpha$ consists essentially of IFN-$\alpha_8$.

3. A method of vaccinating a subject comprising administering to the subject an antigen and interferon (IFN)-$\alpha$ as an adjuvant, wherein the IFN-$\alpha$ consists essentially of IFN-$\alpha_8$ or a mixture of IFN-$\alpha_8$ and IFN-$\alpha_{14}$.

4. A method according to claim 3, wherein the IFN-$\alpha$ consists essentially of IFN-$\alpha_8$.

5. A method according to claim 3, wherein the antigen and the IFN-$\alpha$ are administered separately.

6. A method according to claim 3, wherein the antigen and the IFN-$\alpha$ are administered concurrently.

7. A method according to claim 6, wherein the antigen and the IFN-$\alpha$ are administered as components of the same vaccine composition.

8. A method according to claim 7, wherein the IFN-$\alpha$ consists essentially of IFN-$\alpha_8$.

9. A method for potentiating the proliferation of B cells which comprises contacting the B cells with interferon (IFN)-$\alpha$ under conditions suitable to stimulate such B cells to proliferate, wherein the IFN-$\alpha$ consists essentially of IFN-$\alpha_8$ or a mixture of IFN-$\alpha_8$ and IFN-$\alpha_{14}$.

10. A method according to claim 9, wherein the IFN-$\alpha$ consists essentially of IFN-$\alpha_8$.

* * * * *